(12) United States Patent
Aliyev et al.

(10) Patent No.: US 8,481,444 B2
(45) Date of Patent: Jul. 9, 2013

(54) CATALYST COMPOSITION FOR OLIGOMERIZATION OF ETHYLENE OLIGOMERIZATION PROCESS AND METHOD FOR ITS PREPARATION

(75) Inventors: Vugar Aliyev, Riyadh (SA); Fuad Mosa, Riyadh (SA); Mohammed Al-Hazmi, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 374 days.

(21) Appl. No.: 12/735,072

(22) PCT Filed: Nov. 13, 2008

(86) PCT No.: PCT/EP2008/009585
§ 371 (c)(1),
(2), (4) Date: Jun. 10, 2010

(87) PCT Pub. No.: WO2009/074203
PCT Pub. Date: Jun. 18, 2009

(65) Prior Publication Data
US 2010/0292423 A1    Nov. 18, 2010

(30) Foreign Application Priority Data
Dec. 12, 2007   (EP) .................................... 07024098

(51) Int. Cl.
*B01J 31/04* (2006.01)
*C07C 2/22* (2006.01)

(52) U.S. Cl.
USPC ........... 502/111; 502/103; 502/104; 502/117; 585/502; 585/520; 585/521; 585/522; 585/523

(58) Field of Classification Search
USPC .................. 502/103, 104, 111, 117; 585/502, 585/520, 521, 522, 523
See application file for complete search history.

(56) References Cited

U.S. PATENT DOCUMENTS

| 3,257,332 | A | * | 6/1966 | Ziegler et al. ................. 502/117 |
| 3,576,762 | A | * | 4/1971 | Maguet-Martin et al. .... 502/184 |
| 3,803,105 | A | * | 4/1974 | Galli et al. .................. 526/125.8 |
| 4,434,312 | A | * | 2/1984 | Langer, Jr. .................... 585/523 |
| 4,442,309 | A | * | 4/1984 | Langer, Jr. .................... 585/523 |
| 4,513,095 | A | * | 4/1985 | Speca ........................... 502/111 |
| 4,783,573 | A |   | 11/1988 | Shiraki et al. |
| 5,260,500 | A |   | 11/1993 | Shiraki et al. |
| 2002/0147375 | A1 |   | 10/2002 | Tembe et al. |

FOREIGN PATENT DOCUMENTS

| DE | 4338414 C1 | 3/1995 |
| EP | 0953556 A | 11/1999 |
| EP | 1759766 A | 3/2007 |
| WO | WO 8000224 A1 | 2/1980 |

OTHER PUBLICATIONS

Kominami, et al., "Hydrolysis of Titanium Alkoxide in Organic Solvent at High Temperatures: A New Synthetic Method for Nanosized, Thermally Stable Titanium(IV) Oxide" in Ind. Eng. Chem. Res., 1999, 38, 3925-3931—month unknown.*

* cited by examiner

*Primary Examiner* — In Suk Bullock
*Assistant Examiner* — Bradley Etherton
(74) *Attorney, Agent, or Firm* — Cantor Colburn LLP

(57) ABSTRACT

Catalyst composition for the oligomerization of ethylene, comprising (i) an at least partially hydrolyzed transition metal compound, obtainable by controlled addition of water to a transition metal compound having the general formula $MX_m(OR')_{4-m}$ or $MX_m(OOCR')_{4-m}$, wherein R' is an alkyl, alkenyl, aryl, aralkyl or cycloalkyl group, X is halogen, preferably Cl or Br, and m is from 0 to 4; preferably 0-3; and (ii) an organoaluminum compound as a cocatalyst, wherein the molar ratio of water and transition metal compound is within a range of between about (0.01-3):1; a process for oligomerization of ethylene and a method for preparing the catalyst composition.

19 Claims, No Drawings

CATALYST COMPOSITION FOR OLIGOMERIZATION OF ETHYLENE OLIGOMERIZATION PROCESS AND METHOD FOR ITS PREPARATION

The present invention relates to a catalyst composition for oligomerization of ethylene, a process for preparing linear alpha-olefins by oligomerization of ethylene, as well as to a method for preparing the catalyst composition.

Linear alpha-olefins having 4 to 20 carbon atoms are key feedstocks in the production of surfactants, plastisizers, synthetic lubricants and polyolefins. High purity alpha-olefins are particularly valuable in the production of low-density polyethylene and in the oxo process. The linear alpha-olefins are more reactive than the branched alpha-olefins; the branching at the α-carbon decreases the reactivity drastically. In this regard, linear alpha-olefins having 6 to 18 carbon atoms, especially having 6 to 10 carbon atoms, are particularly useful and widely used in large quantities.

Although linear olefins are the product of dehydrogenation of linear alkanes, the major portion of such products consists of the internal olefins. Preparation of alpha-olefins is based largely on oligomerization of ethylene.

These linear alpha-olefins are prepared usually by the catalytic oligomerization of ethylene in the presence of a Ziegler-type catalyst. The key factor in ethylene oligomerization is to get the desired selectivity and product distribution. Catalyst and process conditions play an important role in this area.

A catalyst for the oligomerization of ethylene to linear C4-C30 alpha olefins is known including zirconium tetrachloride and organoaluminum compound.

The oligomerization of that known catalyst is usually performed in a medium of hydrocarbon solvents at a temperature of about 100 to about 150° C. and at elevated pressures of 4-8 MPa.

However, the main disadvantages of that known catalyst are the poor solubility of zirconium tetrachloride in hydrocarbon solvents, the severe conditions for operation of the catalyst and its relatively low selectivity. In the course of oligomerization of ethylene, a large amount of wax and up to 3.0 wt % of high molecular polyethylene are formed together with the linear alpha-olefins.

U.S. Pat. No. 4,783,573 discloses a catalytic system based on a zirconium/aluminum complex using anhydrous zirconium chloride with aluminum sesquichloride and triethyl aluminum in dry benzene solvent. These components are stirred under an argon atmosphere over a period of time to form the active catalyst complex. Thiophene is added to the catalyst presumably as a moderator.

Patent examples of oligomerization at 120° C. and 3.4 MPa carried out in dry benzene show an ability to manufacture alpha olefins with long chain lengths, with results as follows: $C_4$—14.9 wt %, $C_6$—15.1 wt %, $C_8$—14.0 wt %, $C_{10}$-$C_{18}$—40.2 wt %, $C_{20+}$—14.2 wt % and wax—1.6 wt %. The disadvantage of the process is a high yield of $C_{20+}$ alpha olefins. Another disadvantage is a high reaction temperature. Hence another disadvantage of the process is benzene which used as a solvent is a known carcinogen.

U.S. Pat. No. 5,260,500 discloses the use of an alcohol (methanol and/or ethanol) as a third component to produce a high-purity alpha-olefin free of contaminant. The disadvantage of this system is a high yield of $C_{20+}$ fraction.

EP 0 953 556 B1 discloses a nickel based catalyst system in that the addition of water to a polar organic liquid serving as a solvent for a catalyst system in a process for oligomerization of ethylene affords higher purity linear alpha-olefin oligomers than those formed in the absence of water. According to the patent in the absence of water the decene fraction was 95.05 weight percent decene-1; in the presence of about 1.0 weight percent water in sulfolane the decene fraction was 95.99 weight percent decene-1.

Further, WO 80/00224 and DE 4338414 also teach a catalyst, which includes a zirconium carboxylate of the general formula $(RCOO)_m ZrCl_{4-m}$ and an organoaluminum compound of the formula $R_n AlX_{3-n}$. The main disadvantages of that catalytic system is the formation of undesired and problematic byproducts such as wax and/or polymer (polyethylene, branched and/or cross-linked PE). Another disadvantage of this catalyst system is the high co-catalyst/activator consumption. The catalyst/co-catalyst ratio is a key parameter that enables the modification of the alpha olefin distribution. The high catalyst/co-catalyst ratio can favor low molecular weight oligomers but at the expense of making branched C10+ fractions.

The formation of wax and/or polymers, even in small amounts, adversely affects the entire technological process on producing oligomers, since by-products not only lower the yield of desired oligomers and its purity, but also reduce the working time of the process equipment, insofar as solid polymer accumulating in the reactors has to be periodically removed, which can be done only by interrupting the oligomerization process and hence, at the expense of lost time of the equipment.

Consequently, there is a great need to develop an improved catalyst system which can provide equivalent or even greater catalytic activity and at the same time allows to eliminate all or at least some of the above mentioned problems and reduces the cost of the final catalyst.

It is therefore an object of the present invention to provide a catalyst composition which overcomes the drawbacks of the prior art, especially a catalyst composition shall be provided resulting in a higher purity of the alpha-olefins produced and at the time minimizing of wax/polymer formation in the reactor. Especially alpha-olefins having 6 to 10 carbon atoms shall be provided.

Additionally, a process for preparing linear alpha-olefins by oligomerization of ethylene shall be provided as well as a method for preparing such a catalyst composition.

The first object is achieved by a catalyst composition for the oligomerization of ethylene, comprising
 (i) an at least partially hydrolyzed transition metal compound, obtainable by controlled addition of water to a transition metal compound having the general formula $MX_m(OR')_{4-m}$ or $MX_m(OOCR')_{4-m}$, wherein R' is an alkyl, alkenyl, aryl, aralkyl or cycloalkyl group, X is halogen, preferably Cl or Br, and m is from 0 to 4, preferably 0-3; and
 (ii) an organoaluminum compound as a cocatalyst,
wherein the molar ratio of water and transition metal compound is within a range of between about (0.01-3):1.

Preferably the molar ratio of water and the transition metal compound is within a range of about (0.1-2): 1.

More preferred, the transition metal compound is a zirconium compound.

Most preferred the zirconium compound is a zirconium carboxylate having the formula $(R^2COO)_m ZrCl_{4-m}$, wherein $R^2$ is an alkyl, alkenyl, aryl, aralkyl or cycloalkyl group, and m is any number within the range of from 0 to 4.

In one embodiment the organoaluminum compound has the general formula $R^1_n AlZ_{3-n}$ or $Al_2 Z_3 R^1_3$, wherein $R^1$ represents an alkyl group having from 1 to 20 carbon atoms, Z represents Cl, Br or I, n is any number within the range $1 \leq n \leq 2$.

The organoaluminum compound is preferably $Al(C_2H_5)_3$, $Al_2Cl_3(C_2H_5)_3$, $AlCl(C_2H_5)_2$ or mixtures thereof. According to a more preferred embodiment of the invention the organo aluminum compound is ethyl aluminum sesquichloride and/or diethyl aluminum chloride.

Additionally, the molar ratio of the organoaluminum compound and the transition metal compound is preferably within a range of from 1:1 to 40:1.

Further preferred is that the transition metal compound is partially hydrolyzed.

According to the invention is also a process for preparing linear alpha-olefins by oligomerization of ethylene in the presence of an organic solvent and an invention catalyst composition.

Also provided is a method for preparing an inventive catalyst composition comprising the steps of:
controlled addition of water to the transition metal compound, wherein the transition metal compound is provided in solution; and
(ii) combining the organoaluminum compound with the solution of the at least partially hydrolyzed transition metal compound.

Preferably, the water in step (i) is added incrementally, preferably dropwise, in a staged or sequenced manner, as water vapor or is added by release from water-containing solids.

Even preferred, during and/or after addition of water the solution is agitated for 1 minute to 60 minutes, preferably 1 minute to about 30 minutes, preferably at ambient temperature.

Surprisingly, it has been found that the controlled addition of water in order to at least partially hydrolyze the transition metal compound, preferably a zirconium compound, can improve the catalyst composition affording alpha-olefins having a higher purity wherein also wax/polymer formation in the reactor has been minimized. Controlled amount of water as a modifier has been used to partially hydrolyze the transition metal compound. Especially the use of the zirconium catalyst precursor in combination with organoaluminum chloride compound as co-catalyst results in a selective oligomerization of ethylene to high purity linear alpha olefins with significant reduction of polymer/wax formation.

Additionally, the catalyst composition also exhibits high activity and productivity and requires relatively smaller amounts of the cocatalyst than catalysts of the prior art in order to produce linear oligomers within a desirable molecular weight range, i.e. $C_4$-$C_{20}$-range, preferably $C_6$-$C_{10}$.

Further, the working time of the process equipment can be extended and costs for removing solid polymer accumulations in the reactors can be decreased. The production run can therefore increased.

For someone skilled in the art it is clear what is meant by the term "partially hydrolyzed". In detail, the transition metal compound is used as starting material, and after addition of water which has to be done very carefully, this transition metal compound will be hydrolyzed, i.e. the alkoxide or carboxylate groups are (at least partly) removed from the metal (probably forming ROH or ROOH leaving groups, respectively). In other words, the molar ratio of water and transition metal compound as disclosed above, is the molar ratio of water which is added in a controlled manner to the transition metal starting compound.

The catalyst composition used in the process for preparing linear alpha-olefins is preferably present in an inert organic solvent. Examples of suitable organic solvents include aromatic hydrocarbon solvents, unsubstituted or substituted with halogens, such as toluene, benzene, xylene, chlorobenzene, dichlorobenzene, chlorotoluene and the like, aliphatic paraffin hydrocarbons, such as pentane, hexane, heptane, octane, nonane, decane and the like, alicyclic hydrocarbon compounds, such as cyclohexane, decahydronaphthalene and the like, halogenated alkanes, such as dichloroethane, dichlorobutane and the like. A mixture of solvents may be used to control the product molecular weight distribution to obtain maximum selectivity to the desired olefin products.

The specific hydrolysis ratio (molar ratio of water to transition metal compound) allows to control the extent of hydrolysis. The hydrolysis ratio affects the rate of the reaction. Further, the mode of addition of water to the solution of the transition metal compound does affect the rate of the hydrolysis. For example, after the addition of water, either flock-like particles are produced instantaneously, or no visible particle formation is seen, depending upon the method of addition.

There are several factors that can affect the hydrolysis rate, for example the nature of the organic group, metal coordination number, functionality of the precursor, etc. The hydrolysis reaction itself may be controlled directly by the quantity of water which is supplied to the transition metal compound and the rate of addition. Water can be supplied incrementally or in a staged or sequenced manner, bulk addition does not lead to the desired reaction, effecting excessive hydrolysis with precipitation of insolubles. There are various methods for adding the water. The preferred one is dropwise while the transition metal compound solution in hydrocarbon is kept under agitation. Agitation time is important in order to have a desirable result. The agitation time can be within the range of from 1 minute to 60 minutes, preferably between about 1 minute to about 30 minutes, preferably at ambient temperature.

Additionally, the water may be added using a nitrogen stream to introduce water vapor into the reaction. Water containing solids, which can be either hydrated or porous materials which have absorbed water, can be used as well.

It is therefore essential for the controlled addition of water that the total amount of water is not added as a bulk, i.e. is not added in one charge, but is carefully added in a controlled way to especially avoid the formation of precipitations.

In one preferred embodiment, the calculated amount of water is added dropwise using a syringe to a solution of the transition metal compound at room temperature. It may be preferably to agitate the mixture while adding the water. Depending on the quantity of water, during the addition of it some white precipitation may be observed due to the hydrolysis. Usually, after agitation no precipitation was observed any longer.

The catalyst composition of the present invention may be utilized in the process for preparing linear alpha-olefins at a reaction temperature of about 50° C. to about 110° C., preferably between about 60° C. and about 100° C.

The Zr metal concentration (in wt %) in the zirconium compound can be varied from 2 weight percent to 10 weight percent, preferably from 3 weight percent to 7 weight percent.

The oligomerization can be carried out under usual reaction conditions with regard to temperature, pressure, etc. as is known for someone skilled in the art.

Additional features and advantages of the present invention will become apparent from the following detailed description of preferred embodiments with regard to the following examples.

EXPERIMENTAL CONDITIONS

All materials were handled in a nitrogen atmosphere using either schlenk techniques or nitrogen filled glove box. Nitrogen and toluene were supplied from a plant source and were dried through an additional bed of molecular sieves, if necessary.

EXAMPLES

The synthesis of zirconium carboxylates are performed by known methods.

Oligomerization of ethylene was performed as follows:

The oligomerization is carried out in an 2 liter stainless steel reactor. The prepared catalyst solution is charged into the reactor. Ethylene was introduced into the reactor until the desired pressure was attained and maintained throughout the reaction at the desired temperature. Introduction of ethylene was continued in an amount necessary to maintain the reaction pressure. After the reaction was continued for 1 hour with maintaining the reaction conditions, the ethylene feeding is interrupted and the reaction was stopped by the addition of about 20 ml of ethanol. After bringing the temperature of the reaction mixture to 10° C., a sample of the solution was collected, by means of a valve situated at the bottom of the reactor and analyzed by gas chromatography to determine the quantity and the type of olefins formed. After eliminating the overpressure of ethylene, the reactor was opened and examined for any possible polymer formation. The yield of $C_4$-$C_6$ fractions were estimated from the Schulz-Flory distribution because they are inevitably lost to some extent in handling the sample.

Example 1

To a solution of $Zr(i-C_3H_7COO)_4$ (1.25 mmol) in toluene (3.25 mL) water was injected dropwise having $H_2O/Zr=0.44$. The mixture was stirred for 15 minutes at room temperature. Then from this solution 0.25 mmol of $Zr(i-C_3H_7COO)_4$ were syringed and added to 200 ml toluene which was placed in a 250 ml round bottom flask. Then neat EASC (Al/Zr=17.5) was added to the mixture. The catalyst solution thus formed was then transferred under a stream of inert gas to the reactor. A reaction was conducted at 80° C. and 30 bar ethylene pressure. The oligomerization time was 60 minutes. 193 g of LAO are formed; a yield of LAO 8465 g LAO/g Zr. Clear liquid was obtained. No wax formation has been observed in the product. Only traces of solid polymer were detected namely in quantities too small to be accurately measured.

Example 2

To a solution of $Zr(i-C_3H_7COO)_4$ (1.25 mmol) in toluene (3.25 mL) water was injected dropwise having $H_2O/Zr=1.08$. The mixture was stirred for 15 minutes. Then from this solution 0.25 mmol of $Zr(i-C_3H_7COO)_4$ were syringed and added to 200 ml toluene which was placed in a 250 ml round bottom flask. Then neat EASC (Al/Zr=17.5) was added to the mixture. The catalyst solution thus formed was then transferred under a stream of inert gas to the reactor. A reaction was conducted at 80° C. and 30 bar ethylene pressure. The oligomerization time was 60 minutes. 173 g of LAO are formed; a yield of LAO 7588 g LAO/g Zr. Clear liquid was obtained. No wax formation has been observed in the product. Only traces of solid polymer were detected namely in quantities too small to be accurately measured.

Example 3

To a solution of $Zr(i-C_3H_7COO)_4$ (1.25 mmol) in toluene (3.25 mL) water was injected dropwise having $H_2O/Zr=1.32$. The mixture was stirred for 15 minutes. Then from this solution 0.25 mmol of $Zr(i-C_3H_7COO)_4$ were syringed and added to 200 ml toluene which was placed in a 250 ml round bottom flask. Then neat EASC (Al/Zr=17.5) was added to the mixture. The catalyst solution thus formed was then transferred under a stream of inert gas to the reactor. A reaction was conducted at 80° C. and 30 bar ethylene pressure. The oligomerization time was 60 minutes. 162 g of LAO are formed; a yield of LAO 7105 g LAO/g Zr. Clear liquid was obtained. No wax/polymer formation has been observed.

Example 4

To a solution of $Zr(i-C_3H_7COO)_4$ (1.25 mmol) in toluene (3.25 mL) water was injected dropwise having $H_2O/Zr=0.44$. The mixture was stirred for 15 minutes. Then from this solution 0.25 mmol of $Zr(i-C_3H_7COO)_4$ were syringed and added to 200 ml toluene which was placed in a 250 ml round bottom flask. Then neat EASC (Al/Zr=35) was added to the mixture. The catalyst solution thus formed was then transferred under a stream of inert gas to the reactor. A reaction was conducted at 80° C. and 30 bar ethylene pressure. Oligomerization time was 60 minutes. 155 g of LAO are formed; a yield of LAO 6798 g LAO/g Zr. Clear liquid was obtained. No wax/polymer formation has been observed.

Example 5

To a solution of $Zr(i-C_3H_7COO)_4$ (1.35 mmol) in toluene (3.25 mL), water was injected dropwise having $H_2O/Zr=0.82$. The mixture was stirred for 15 minutes. Then from this solution 0.25 mmol of $Zr(i-C_3H_7COO)_4$ were syringed and added to 200 ml toluene which was placed in a 250 ml round bottom flask. Then neat EASC (Al/Zr=17.5) was added to the mixture. The catalyst solution thus formed was then transferred under a stream of inert gas to the reactor. A reaction was conducted at 70° C. and 30 bar ethylene pressure. Oligomerization time was 60 minutes. 186 g of LAO are formed; a yield of LAO 8157 g LAO/g Zr. Clear liquid was obtained. No wax/polymer formation has been observed.

Example 6

To a solution of $Zr(i-C_3H_7COO)_4$ (6.25 mmol) in toluene (11 ml) water was injected having $H_2O/Zr=0.68$. The mixture was stirred for 15 minutes. Then from this solution 0.25 mmol of $Zr(i-C_3H_7COO)_4$ were syringed and added to 200 ml toluene which was placed in a 250 ml round bottom flask. Then neat EASC (Al/Zr=17.5) was added to the mixture. The catalyst solution thus formed was then transferred under a stream of inert gas to the reactor. The reaction was conducted at 75° C. and 30 bar ethylene pressure. Oligomerization time was 60 minutes. 245 g of LAO are formed; a yield of LAO 10745 g LAO/g Zr. Clear liquid was obtained. No wax/polymer formation has been observed.

Example 7

The same hydrolyzed zirconium catalyst solution as prepared in Example 6 has been tested after 1 month period using the same procedure as described in Example 6, (the sample was mixed for 1 minute prior taking the required amount) in order to check its reproducibility. In case that the catalyst solution is stored for a longer time, it might be necessary to periodically agitate the solution in order to avoid precipitation to occur. 234 g of LAO are formed; a yield of LAO 10263 g LAO/g Zr. Clear liquid was obtained. No wax/polymer formation has been observed.

Comparative Example 1

200 ml toluene, 0.25 mmol of $Zr(i-C_3H_7COO)_4$ and neat ethyl aluminum sesquichloride (EASC) (Al/Zr=35) were mixed in a 250 ml round bottom flask. The catalyst solution thus formed was then transferred under a stream of inert gas to the reactor. The reaction was conducted at 80° C. and 30 bar ethylene pressure. Oligomerization time was 60 minutes. 213 g of LAO was formed; a yield of LAO 9342 g/g Zr. Traces of solid polymer were observed.

Comparative Example 2

The same procedure as in Comparative Example 1 was repeated, except that Al/Zr=17.5. Reaction was conducted at 80° C. and 30 bar ethylene pressure. Oligomerization time was 60 minutes. 460 g of LAO and 0.2 g of byproduct polyethylene are formed; a yield of 20175 g LAO/g Zr. A high amount of wax was formed which could not be correctly analysed by GC.

Comparative Example 3

The same procedure as in Comparative Example 1 was repeated, except toluene was spiked with defined amount of water, having 20 ppm of water in toluene. 153 g of LAO was formed; a yield of LAO 6710 g/g Zr. The experimental result showed that the product purity decreased dramatically (mainly due to Friedel-Crafts alkylation of toluene). A significant increase in polymer formation was observed as well, which mainly deposited on the reactor wall, stirrer and thermowell.

Table 1 below summarizes the distribution of the chain length of the alpha-olefins obtained, whereas table 2 below summarizes the purity of the LAO-fraction obtained.

TABLE 1

Summary of the Oligomerization Experiments

| Examples | Distribution of alpha olefins (wt %) | | | |
|---|---|---|---|---|
| | C4 | C6-C10 | C12-C18 | C20+ |
| Example1 | 19.3 | 61.8 | 16.8 | 2.1 |
| Example2 | 23.9 | 60.9 | 13.4 | 1.8 |
| Example3 | 26.3 | 58 | 14.2 | 1.5 |
| Example4 | 40.2 | 49.3 | 10 | 0.5 |
| Example5 | 26.4 | 56 | 16.4 | 1.2 |
| Example6 | 23.9 | 57.4 | 16.6 | 2.1 |
| Example7 | 26.4 | 54.9 | 16.2 | 2.5 |
| Comparative Example 1 | 35.1 | 45.8 | 17.4 | 1.7 |
| Comparative Example 2 | 15 | 30.4 | 40.9 | 13.7 |
| Comparative Example 3 | 35.5 | 40.3 | 21.4 | 2.8 |

TABLE 2

| Examples | Purity of LAO fractions (%) | | | | | | | | |
|---|---|---|---|---|---|---|---|---|---|
| | C4 | C6 | C8 | C10 | C12 | C14 | C16 | C18 | Total Aromatics (wt %) |
| Example1 | 99.7 | 97.4 | 96.8 | 94.1 | 93.7 | 92.9 | 91.8 | 90.7 | 0.35 |
| Example2 | 99.6 | 98 | 96.3 | 95 | 95.2 | 93.4 | 92.2 | 91.5 | 0.2 |
| Example3 | 99.3 | 98.2 | 97.3 | 96.7 | 96.8 | 94.1 | 93.5 | 92.8 | 0.27 |
| Example4 | 98.2 | 97.2 | 97.6 | 90.4 | 90.5 | 86.1 | 85 | 81.8 | 0.21 |
| Example5 | 98.8 | 98.7 | 97.8 | 95.4 | 94.3 | 93.9 | 92 | 91.7 | 0.4 |
| Example6 | 99 | 98 | 96.5 | 95.8 | 94.9 | 93.5 | 92.8 | 93.7 | 0.5 |
| Example7 | 99.3 | 98.4 | 96.3 | 95.5 | 94.3 | 93.6 | 92.4 | 93 | 0.3 |
| Comparative Example 1 | 98.2 | 96.1 | 95 | 88.2 | 86 | 85.4 | 84.7 | 80.3 | 0.47 |
| Comparative Example 2 | 98.1 | 97.1 | 94.8 | 91.1 | 90.5 | 87.2 | 79.1 | 77.4 | 0.7 |
| Comparative Example 3 | 97.3 | 95.4 | 93.8 | 85.7 | 84.6 | 80.3 | 75.9 | 72.3 | 2.1 |

As can be seen from above tables, the catalyst composition according to present invention results in a distribution of alpha-olefins having a high amount of desired $C_6$-$C_{10}$ alpha-olefins. As can be taken from table 2 the purity of the fractions obtained by the catalyst composition according to the present invention is also significantly improved.

The features disclosed in the foregoing description and in the claims may, both separately and in any combination thereof, the material for realizing the invention in diverse forms thereof.

The invention claimed is:

1. A catalyst composition for the oligomerization of ethylene, comprising:
   (i) An at least partially hydrolyzed transition metal compound comprising the hydrolyazation product of a transition metal compound having the general formula $MX_m(OOCR')_{4-m}$, wherein M is a transition metal, R' is an alkyl, alkenyl, aryl, aralkyl or cycloalkyl group, X is halogen, and m is from 0 to 3; and
   (ii) An organoaluminum compound as a cocatalyst, wherein the molar ratio of water to transition metal compound is within a range of between about 0.1:1 to about 3:1.

2. The catalyst composition according to claim 1, wherein the molar ratio of water to the transition metal compound is within a range of between about 0.1:1 to about 2:1.

3. The catalyst composition according to claim 2, wherein the transition metal compound comprises a zirconium carboxylate having the formula $(R^2COO)_mZrCl_{4-m}$, wherein $R^2$ is an alkyl, alkenyl, aryl, aralkyl or cycloalkyl group, and m is an integer within the range of from 0 to 3.

4. The catalyst composition according to claim 3, wherein the zirconium carboxylate comprises $Zr(i-C_3H_7COO)_4$.

5. The catalyst composition according to claim 4, wherein the organoaluminum compound is $Al(C_2H_5)_3$, $Al_2Cl_3(C_2H_5)_3$, $AlCl(C_2H_5)_2$ or mixtures thereof, and the molar ratio of the organoaluminum compound to the transition metal compound is within a range of from 1:1 to 40:1.

6. The catalyst composition according to claim 3, wherein the organoaluminum compound has the general formula $R^1{}_nAlZ_{3-n}$ or $Al_2Z_3R^1{}_3$, wherein $R^1$ represents an alkyl group having from 1 to 20 carbon atoms, Z represents Cl, Br or I, and n is an integer within the range $1 \leq n \leq 20$.

7. The catalyst composition according to claim 6, wherein the zirconium carboxylate is $Zr(i-C_3H_7COO)_4$ which is hydrolyzed by the dropwise addition of water and the molar ratio of the organoaluminum compound to the zirconium compound is within the range of from 1:1 to 40:1.

8. A process for the oligomerization of ethylene, comprising contacting ethylene with the catalyst composition of claim 7 under ethylene oligomerization conditions.

9. The catalyst composition according to claim 6, zirconium carboxylate comprises $Zr(i-C_3H_7COO)_4$.

10. The catalyst composition according to claim 9, wherein the zirconium carboxylate is partially hydrolyzed by the dropwise addition of water.

11. The catalyst composition according to claim 9, wherein the molar ratio of the organoaluminum compound to the zirconium carboxylate is within the range from 1:1 to 40:1.

12. A process for the oligomerization of ethylene, comprising contacting ethylene with the catalyst composition of claim 11 under ethylene oligomerization conditions.

13. A method for preparing a zirconium carboxylate catalyst composition, consisting essentially of the steps of:
   (i) creating a solution of a zirconium carboxylate compound in an organic solvent;
   (ii) at least partially hydrolyzing the zirconium carboxylate compound by adding water to the compound in a controlled manner; and
   (iii) combining an organoaluminum compound with the solution of the at least partially hydrolyzed zirconium carboxylate compound.

14. The method according to claim 13, wherein the water in step (ii) is added incrementally to the zirconium carboxylate compound by dropwise addition to the zirconium carboxylate compound solution while it is under agitation.

15. The method according to claim 14, wherein the zirconium carboxylate compound comprises $Zr(i-C_3H_7COO)_4$ and the zirconium carboxylate solution is agitated for 1 minute to 60 minutes during and/or after the additon of the water to the solution.

16. The method according to claim 13, wherein the water in step (ii) is added incrementally to the zirconium carboxylate compound by release from a water-containing solid.

17. The method according to claim 16, wherein the zirconium carboxylate compound comprises $Zr(i-C_3H_7COO)_4$.

18. The method according to claim 13, wherein the water in step (ii) is added incrementally to the zirconium carboxylate compound as water vapor in a gas stream.

19. The method according to claim 18, wherein the zirconium carboxylate compound comprises $Zr(i-C_3H_7COO)_4$.

* * * * *